United States Patent [19]

Leaseburge et al.

[11] Patent Number: 4,580,759

[45] Date of Patent: Apr. 8, 1986

[54] MULTIPLE PORT, SLIDING PLATE VALVE

[75] Inventors: Emory J. Leaseburge, Lewisburg; Curtis L. Perkins, Ronceverte, both of W. Va.

[73] Assignee: Combustion Engineering, Inc., Windsor, Conn.

[21] Appl. No.: 640,275

[22] Filed: Aug. 13, 1984

[51] Int. Cl.$^4$ ............................................. F16K 11/06
[52] U.S. Cl. ...................................... 251/62; 251/174; 137/625.48
[58] Field of Search ................ 251/62, 111, 176, 193, 251/174, 195, 204, 326; 137/625.48, 625.38, 625.49, 625.68

[56] References Cited

U.S. PATENT DOCUMENTS

| | | | |
|---|---|---|---|
| 2,860,660 | 11/1958 | Swatsworth | 137/625.48 |
| 3,222,028 | 12/1965 | Grove | 251/176 |
| 3,415,282 | 12/1968 | Zoludow | 137/625.48 |
| 3,521,674 | 7/1970 | Dodson et al. | 137/625.48 |
| 3,570,540 | 3/1971 | McInnes et al. | 137/625.48 |
| 3,589,380 | 6/1971 | Gastinne | 251/326 |
| 3,774,639 | 11/1973 | Commarmot | 137/625.48 |
| 3,820,828 | 6/1974 | Fiddler | 137/625.48 |
| 3,933,165 | 1/1976 | Budzak et al. | 137/625.48 |
| 3,980,102 | 9/1976 | Kiesow | 137/625.48 |
| 4,334,552 | 6/1982 | Blanchard | 137/625.48 |
| 4,448,390 | 5/1984 | Halstead et al. | 137/625.48 |
| 4,493,476 | 1/1985 | Strickland et al. | 251/176 |
| 4,532,960 | 8/1985 | Brunner | 137/625.68 |

FOREIGN PATENT DOCUMENTS

| | | | |
|---|---|---|---|
| 1905365 | 10/1969 | Fed. Rep. of Germany | 137/625.48 |
| 845187 | 8/1960 | United Kingdom | 137/625.48 |

Primary Examiner—Margaret A. Focarino
Assistant Examiner—H. A. Odar
Attorney, Agent, or Firm—Troxell K. Snyder

[57] ABSTRACT

A sliding plate valve for a gas chromatograph or the like is provided with a pneumatic actuator (22) for reciprocating a slider assembly (24) and slide pad (26) over the face surface (28) of the valve body (20). Flow passages (44) are aligned with flow openings (42) in the face surface (28) as the slide pad (26) reciprocates between purge and sample positions. The slide pad (26) is urged against the face surface (28) by force springs (60) which are movable with the reciprocating slider housing (64). The slide pad (26) and assembly (24) are maintained in alignment by the interaction of chamfered grooves (68, 70) and chamfered lip surfaces (76, 78).

7 Claims, 2 Drawing Figures

MULTIPLE PORT, SLIDING PLATE VALVE

FIELD OF THE INVENTION

The present invention relates to a multiple port, sliding plate valve for directing a plurality of flow streams, and more particularly, to a multiple port, sliding plate sample valve for directing a plurality of purge and sample material flow streams to a chromatograph analyzer.

BACKGROUND OF THE INVENTION

It is well known in the valve art to supply valves for the introduction of a sample volume of material for analysis testing or other purposes. One type of composition analysis system which uses sampling valves is chromatography, wherein a liquid or gas of unknown composition is introduced at one end of a packed column containing a diffusing medium. For a multiple component gas or liquid stream, each component will diffuse through the medium at a different rate, emerging at the other end of the column at different elapsed times from introduction.

The composition of an unknown gas stream is typically measured by first purging the column with a pure carrier gas, introducing a measured sample of the subject gas stream at the entrance end of packed column, and measuring the elapsed time and volume of each emergence of noncarrier gas components from the exit end of the packed column. Based upon past experience with various types of diffusing media, one skilled in the chromatography art may accurately determine both the identity and mole fraction of the components of the subject gas stream.

It should be apparent from the foregoing discussion that the accuracy of the final component measurement is dependent upon the introduction of a precise amount of the subject gas stream at the appropriate time. Sample valves developed for this use have been adapted to establish not only the flow of carrier gas into the diffusing medium, but to also maintain a precise volume of the subject gas or liquid ready for introduction to the packed column upon demand.

A typical sample valve for such an application is actuable between a purge mode and an injection mode. In the purge mode, the valve maintains a flow of carrier gas through the diffusing medium while simultaneously causing a flow of the subject gas or liquid to pass through a sample loop of preselected volume. Upon actuation of the valve into the inject mode, the flow stream of carrier gas is redirected through the sample loop pushing the temporarily trapped volume of subject gas into the inlet of the packed column and through the diffusing medium.

As will be appreciated by those skilled in the art, such a transfer requires redirection of a plurality of gas or liquid flow streams in a precise and timely fashion. Moreover, as the amount of subject gas injected must be precisely controlled, it is further apparent that any type of leakage or other sample loss will adversely affect the accuracy of the final gas readings. Leakage of carrier gas or liquid into the sample loop prior to actuation of the sample valve will likewise affect analysis accuracy.

The chromatograph sample valves of the prior art are typically of the sliding plate type, wherein a movable plate having a plurality of flow passages disposed therein is reciprocated over a corresponding surface or surfaces having a plurality of flow openings disposed therein. Depending upon the particular position of the sliding plate, various flow openings may be placed in fluid communication for transferring flowing material therebetween.

Two functions are central to the successful operation of a sliding plate valve for this type of service. First the sliding plate and corresponding surface must be maintained in a sealing relationship, typically accomplished by urging the plate and surface together by the use of springs or other urging means. It will be appreciated by those skilled in the art that such urging force must be uniformly distributed over the sliding plate, so as to prevent the possibility of uneven wear and/or leakage between the plate and surface. Second, it is necessary to maintain the flow passages and flow openings in substantially accurate alignment during each actuation of the sample valve. Any misalignment would clearly result in partially obstructed, totally obstructed, or misdirected fluid communication between the flow openings. It should also be noted that the parts in sliding contact, i.e., the plate and surface, will experience frictional wearing during extended periods of operation, requiring the replacement or repair of either one or both members.

Sliding plate valves known in the prior art typically use springs mounted on the valve body or other fixed urging means to press the sliding plate against the corresponding face surface in a sealing relationship. Such an arrangement has proved less than satisfactory, particularly when the sliding plate is reciprocated between positions, moving relative to the fixed urging springs and experiencing variations in force distribution. Such variations may lead to uneven plate wear and leakage.

Alignment of the sliding plates in valves of the prior art is also a potential problem. Typically, prior art valves confine this motion of the sliding plate between fixed or adjustable side rails which can be subject to misalignment or wear. For compact sample valves having numerous, closely spaced flow openings and passages, the margin of error due to misalignment of the corresponding flow openings and passages is very small, requiring frequent servicing to maintain valve performance.

it is also the nature of process gas chromatography that the chromatograph analyzer be placed adjacent the gas stream being analyzed, often in locations remote from the process operator, and in a hostile environment. It is therefore desirable to minimize the frequency of replacing or repairing worn parts in such an analyzer, as well as reducing the amount of time necessary to effect such repairs. Another drawback of the sample valve designs in the prior art is that in order to replace the sliding plate, typically the component wearing out most frequently, it is necessary to disassemble the valve and urging means in order to release and gain access to the sliding plate.

An improved sliding plate valve over those known in the present art would therefore include enhanced means for uniformly and constantly urging the sliding plate into sealing contact with the face surface, aligning the sliding plate flow passages and the face surface flow openings during the actuation of the valve, and be well adapted for simple, quick replacement of wearing parts.

SUMMARY OF THE INVENTION

The present invention provides a sliding plate valve wherein the slide plate, or pad, is constantly and uniformly pressed against the valve body face surface throughout the entire range of motion. The pressing mechanism is integrated with the slide support housing and moves with the slider assembly during reciprocation between positions. The constant and uniform pressure exerted enhances the reliability of the sealing relationship between the slide pad and the face surface, reducing the likelihood of undesirable leaking or other failure.

It is also a feature of the present invention to provide a means for maintaining the alignment of the slide pad relative to the face surface throughout the reciprocal motion identified above. In one embodiment, a pair of opposing lips extending from the slide housing engage a pair of corresponding grooves in the valve body for allowing linear sliding movement therebetween, but preventing vertical separation under the influence of a compressed spring acting to press the slide against the face surface of the valve body. The lips and grooves are correspondingly chamfered to induce the slider assembly to be self-centering with respect to the face surface, thus insuring proper matchup of the flow openings in the face surface and the flow passages in the slide pad.

It is still further a feature of the valve according to the present invention to provide a slide pad easily removable for service and possible replacement as required by operating circumstances. To this end, the present invention includes means for releasing both the urging force applied to the slide pad against the face surface and the coupling between the slider assembly and the actuator inducing the reciprocal motion thereof. Upon such release, the slider assembly of the preferred embodiment valve may be manually disengaged from the valve body and conveniently serviced by maintenance personnel.

BRIEF DESCRIPTION OF THE DRAWING FIGURES

DESCRIPTION OF THE PREFERRED EMBODIMENT

Figure 1:
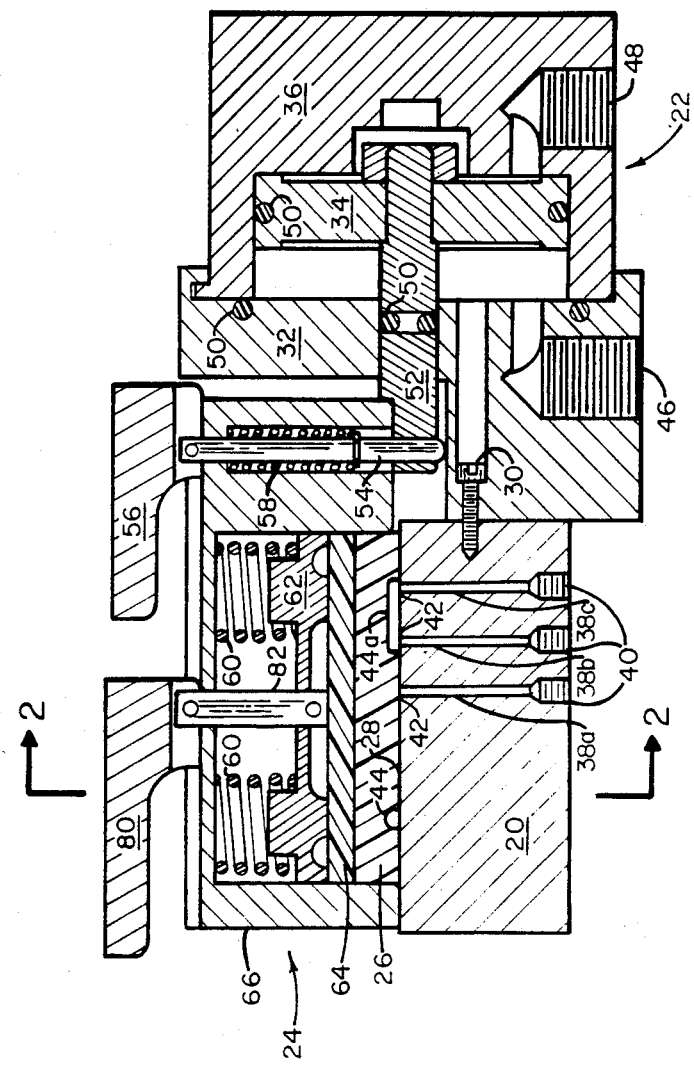
FIG. 1 is a sectional side view of the valve according to the present invention.

Turning now to the drawing figures, and in particular FIG. 1, the preferred embodiment of the present invention will now be described.

The present invention consists of a valve body 20, an actuator designated generally as 22, and a slider assembly 24 enclosing and supporting the slide pad 26 which contacts a planar face surface 28 of the valve body 20.

Disposed within valve body 20 are shown a plurality of flow conduits, designated generally 38 which are shown communicating between threaded external connections 40 on one end to openings 42 shown disposed in the face surface 28 of the valve body 20.

In operation in a gas chromatograph analyzer, a sample valve according to the present invention would be coupled to the carrier gas stream and the subject gas stream through external tubing (not shown) connected to the threaded connectors 40. Slide pad 26 is pressed firmly against the planar face surface 28 for establishing and maintaining a sealing relationship between the pad 26 and the face surface 28.

During operation, flow passages 44 in the pad 26 are caused to line up with flow openings 42 in the face surface 28, thus establishing fluid communication between two or more flow conduits 38. Referring specifically to FIG. 1 and the conduits 38a, 38b, 38c, it can be seen in FIG. 1 that passage 44a has established fluid communication between flow conduits 38b and 38c. During actuation of the valve according to the present invention, slider assembly 24 moves to the left relative to valve body 20 causing flow passage 44a to then establish fluid communication between conduits 38a and 38b.

The exact nature and number of such switching operations which occur during the movement of the slider assembly 24, and hence the slide pad 26, is related to the number of flow conduits 38 and flow passages 44 disposed in the respective valve body 20 and pad 26. In the preferred embodiment of the present invention, the slide is reciprocated between two positions by means of the actuator 22, shown secured to the valve body 20 by screw means 30 or the like.

The actuator of the preferred embodiment is pneumatic, comprising a base plate 32, secured to the valve body 20 by securing means 30, cylinder 36, releasably connected to the base 32, and piston 34 disposed within the cylinder 36. The piston 34 is reciprocable within the cylinder 36 under the influence of hydraulic pressure applied to the appropriate pressure ports 46, 48. Sealing means 50 disposed about the piston 34 and the piston arm 52 prevent leakage of the hydraulic fluid supplied to pressure ports 46, 48. Sealing means 50 may be any of a variety of surface and sliding seals known in the art, such as resilient O-rings as shown in FIG. 1.

The slider assembly 24 is secured to the actuator arm 52 by a spring loaded locking pin 54. The locking pin 54 fits within a matching hole disposed in the actuator arm 52 and causes the reciprocation of the slider assembly 24 under the influence of the actuator 22. The slider assembly is releasable from the actuator arm 52 by raising the locking pin cam 56, withdrawing the locking pin 54 against the locking spring 58, thus withdrawing the locking pin 54 from the corresponding hole in the actuatior arm 52.

Figure 2:
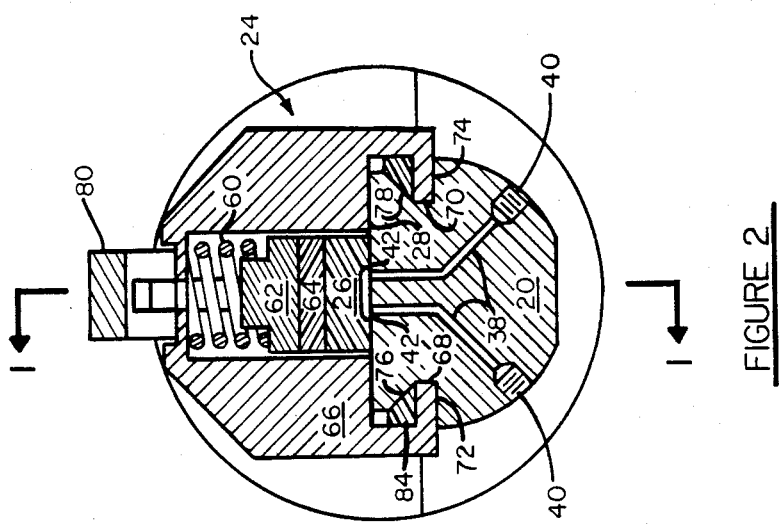
FIG. 2 is a sectional end view of the valve as indicated in FIG. 1.

The remaining portion of the slider assembly 24 will be disclosed with reference to both FIGS. 1 and 2. FIG. 1 shows clearly how the slide pad 26 is urged against the valve body 20 by means of the force springs 60 and the rigid backing plate 62. Between the rigid backing plate 62 and the slide pad 26 is a cushion pad 64 for more evenly distributing the force of the rigid backing plate 62 against the pad 26. The use of the cushion pad 64, typically fabricated of silicon rubber sheet or the like, has been found to enhance the reliability and integrity of the seal formed between the pad 26 and the face surface 28, and its use is herein disclosed in partial fulfillment of the Applicant's duty of disclosure of the best mode of practicing the present invention.

Force springs 60 in FIG. 1 clearly are compressed between the slider housing 66 and the backing plate 62. FIG. 2 discloses the use of a pair of opposing grooves 68, 70 disposed in the valve body 20 parallel to the direction of motion of the pad 26 and slider assembly 24 during reciprocation. Slider housing 66 can be seen to include a pair of inward facing lips 72, 74 which fit within the grooves 68, 70 for restraining the slider assembly from vertical motion relative to the face surface 28.

The contacting surfaces 76, 78 of the opposing lips 72, 74 and the grooves 68, 70 are chamfered so as to cause the slider assembly 24 to remain centered relative to the valve body 20 during movement of the slider housing 66. The force exerted by force springs 60 thus moves with the backing plate 62 and hence the slide pad 26 as the pad 26 and slider assembly 24 reciprocate between positions, thus resulting in a uniform and constant application of sealing force between the pad 26 and face surface 28.

Moreover, the chamfered surfaces 76, 78 of the respective lips 72, 74 and grooves 68, 70 serve not only to restrain the slider housing 66 and hence the force springs 60 against the face surface 28, but also serve to cause the slider assembly 24 and pad 26 to remain centered on the face surface 28 during operation of the sample valve according to the present invention. It will also be appreciated by those skilled in the art that the chamfered surfaces 76, 78 are able to incur a significant amount of wear without degradation of the alignment function. As the lips 72, 74 or grooves 68, 70 wear down, the slider housing 66 moves away from the valve body 20 under the influence of the force springs 60. By utilizing replaceable insert blocks 84, 86, fabricated of a synthetic resin polymer such as TEFLON or the like, wear in the preferred embodiment is confined to the blocks 84, 86 and may be easily corrected by replacement during removal of the slider assembly 24 as discussed hereinbelow.

The urging force supplied by force springs 60 against the restraining plate 62 may be withdrawn, releasing the slider assembly 24 by lifting cam 80, thus pulling retracting bar 82 into the slider housing 66 and compressing the backing plate 62 further against force springs 60. With both cams 80, 56 lifted, and the urging force removed from the pad 26 and the locking pin 54 withdrawn from engagement with the actuator arm 52, the slider assembly 24 is free to be moved completely off the left hand portion of the valve body 20 as seen in FIG. 1. The disassembled sample valve according to the present invention may be serviced quite readily, particularly with regard to the replacement of the slide pad 26. The slide pad 26 is easily removed and replaced with a fresh, unworn pad. The slider assembly 24 is then quickly and easily replaced by aligning the lips 72, 74 with the grooves 68, 70, and sliding the assembly 24 back into the proper position. After lowering cams 80, 56, thus restoring the urging force from force springs 60 and re-engaging the slider assembly 24 with the actuator 22, the valve is again ready for service.

In terms of materials of construction, the rigid portions of the valve of the preferred emodiment may be constructed of stainless steel, carbon steel, Hastalloy, or other material as necessary to withstand the particular environment and fluids being sampled. The slide pad 26 may also be made of a variety of materials, preferably a synthetic resin polymer or the like, such as TEFLON or RULON. The overriding concern in the choice of materials for the slide pad 26 and the valve body 20 is that the materials selected be able to form a sliding seal between the pads 26 and the valve body face surface 28, and that, preferably, frictional wear be confined to the pad 26.

The valve according to the present invention thus insures constant, uniform pressure between the slide pad and the face surface of the valve body by incorporating the urging means into a slider assembly movable with the pad over the face surface. The present invention also includes means for maintaining the alignment of the pad and the flow openings disposed in the face surface of the valve body and means for easily releasing the slider assembly for removal and repair.

Both these advantages and others will apparent to one skilled in the art upon review the foregoing specification and the appended claims and drawing figures. It should also be noted that, although the urging means within the slider assembly is disclosed herein as being a compressed coil spring, and that the actuator means 22 in the preferred embodiment is disclosed as a linearly reciprocable pneumatic piston, the present invention includes all urging means and actuators known in the art, including but not limited to hydraulic, electromechanical, electromagnetic, gravitational, tortional, or the like.

We claim:

1. A sliding plate, multiple port valve, comprising:
a valve body having a planar face surface, said face surface having a plurality of openings disposed therein, each of the openings in fluid communication with an individual port of said valve;
a slide pad, slidable over the face surface and engaged therewith in a sealing relationship, said pad including a flow passage therein for establishment of fluid communication between a plurality of selected flow openings when said pad is in a first position relative to the face surface;
means for urging said pad into said sealing relationship with the face surface, the urging means being movable with said pad for maintaining a constant urging force thereagainst, the urging means further including
a slider housing for enclosing said pad, the housing further including a spring internal to the housing for urging said pad against the face surface, and
means for restraining the housing from motion away from the valve body, said restraining means further allowing linear reciprocating motion of the housing and providing means for aligning said pad with the plurality of selected flow openings when said pad is in the first position, the restraining and aligning means further including
two grooves, disposed in the valve body, said grooves each being adjacent opposite sides of the face surface, colinear with the desired motion of the pad, and opening in opposite directions, each groove further having the inner surface proximate the face surface sloped in relation thereto, and
two engaging lips, secured to the slider housing in an opposing relationship, each lip configured to slidably engage the corresponding groove in the valve body for restraining and aligning the housing and hence said pad; and
an actuator, operable between said pad and the valve body, for reciprocating said pad between the first position and a second position relative to the face surface.

2. The valve as recited in claim 1, further comprising:
means for removing the tension of the spring within the housing, and
means for releasing the actuator from the pad, whereby the housing and pad may be removed from the valve body.

3. A multiple port switching valve, comprising:
a valve body having a planar face surface, the face surface having a plurality of flow openings disposed therein;
a pad, slidable over the face surface, having a flow passage for establishment of fluid communication between at least two of the flow openings in the face surface;

an actuator, secured to the valve body, having a movable arm reciprocable between a first position and a second position; and a movable slider housing, supporting said pad and releasably secured to the actuator arm, said slider housing including means for urging said pad into a sealing relationship with the face surface and means for maintaining alignment of said pad on the face surface during reciprocation, the means for maintaining alignment of said pad including two opposing lips, each lip being slidably engaged with a corresponding groove in the valve body for preventing separation of the slider and the valve body while permitting linear motion therebetween, each lip and groove further being chamfered for maintaining a preferred alignment between the face surface and said pad subsequent to occurrence of any wear of the lips or grooves.

4. The valve of claim 3, wherein the urging means includes a support plate disposed adjacent said pad opposite the face surface and a spring, compressed between the support plate and the slider housing.

5. The valve of claim 4, further comprising:

a retracting bar, secured to the support plate and extending through the housing, and a retracting cam, connected to the outer end of said retracting bar for retracting the support plate against the spring, removing the urging force from the pad.

6. A sliding plate sample valve for selectively directing a plurality of flow streams, comprising:

a valve body having a planar face surface, the surface including a plurality of flow openings disposed therein;

a pad, linearly reciprocable between a first position and a second position, said pad further including at least one flow passage disposed therein for establishing fluid communication between at least two of the flow openings disposed in the face surface when said pad is in the first position;

means for urging said pad into a sealing relationship with the face surface during reciprocation of said pad, said urging means being movable with the pad;

means for maintaining said pad in alignment with the flow openings disposed in the face surface during reciprocation of said pad;

an actuator for selectively reciprocating said pad between the first and second positions;

a slider housing, supporting the pad and reciprocating therewith, the slider housing enclosing said urging means and including means for selectively cancelling the function of said urging means; and means for releasably coupling the actuator to the slider housing; whereby the slider housing and hence said pad may be removed from the valve body upon cancellation of the function of said urging means and release of the coupling means, the valve body further including a pair of oppositely opening grooves, disposed in the valve body on opposite sides of the face surface and oriented colinearly with the motion of the pad and the slider housing, each groove opening into a plane oriented both perpendicular to the face surface and parallel to the motion of said pad and slider housing, and the portion of each groove nearest the face surface further being chamfered outwardly theretowards, the alignment means further including a pair of oppositely facing lips, extending from the slider housing, each lip slidably engaging the corresponding groove in the valve body, a portion of each lip engaging the chamfered portion of the corresponding groove and each being likewise chamfered for forming a close fit therebetween; and the urging means further comprising a spring, disposed and compressed between the slider housing and said pad, for exerting and urging force on the pad against the face surface and for exerting a resultant force on the slider housing in an upward direction away from the face surface, thereby resulting in an alignment force due to the cooperative action of the chamfered groove surfaces and the chamfered lip portions as the slider housing is restrained from motion away from the valve body under the influence of said resultant force.

7. The valve of claim 6, wherein the means for releasing the urging means further comprises a relatively inflexible support plate, disposed between the pad and the spring, a retracting bar, secured to the support plate at a first end and extending upwardly through the slider housing, and a retracting cam lever, attached to the second end of the retracting bar approximate the slider housing for withdrawing the retracting bar and support plate away from said pad, the actuator further includes an arm, extending between the actuator and the slider housing for causing the reciprocal motion of the slider housing, and an elongated locking pin, oriented transversely to the direction of motion of the slider housing and typically engaged between the housing and the actuator arm for coupling the arm and slider housing, said elongated pin being movable to a withdrawn position not engaged with the arm, thereby resulting in the release of the coupling means.

* * * * *